(12) United States Patent
Bader

(10) Patent No.: US 7,749,423 B2
(45) Date of Patent: Jul. 6, 2010

(54) METHOD OF PRODUCING AN ORTHOTIC BRACE OR PROSTHETIC DEVICE

(76) Inventor: Wade Bader, 13711 N. Dale Mabry Hwy., Tampa, FL (US) 33618

( * ) Notice: Subject to any disclaimer, the term of this patent is extended or adjusted under 35 U.S.C. 154(b) by 943 days.

(21) Appl. No.: 11/236,254

(22) Filed: Sep. 27, 2005

(65) Prior Publication Data

US 2007/0073202 A1    Mar. 29, 2007

(51) Int. Cl.
*B32B 9/00* (2006.01)
(52) U.S. Cl. .................. 264/511; 264/101; 264/102; 264/220; 264/222; 264/257; 264/259; 264/266; 264/319
(58) Field of Classification Search .............. 602/8, 602/27; 264/101, 511, 510, 241, 102, 220, 264/222, 257, 259, 266, 319; 156/285, 242
See application file for complete search history.

(56) References Cited

U.S. PATENT DOCUMENTS 5,158,530 A * 10/1992 Conklin ................. 602/8
5,458,656 A * 10/1995 Phillips .................. 623/27
5,573,501 A * 11/1996 Ruscito et al. ............ 602/7
6,394,971 B1 * 5/2002 Slautterback et al. ...... 602/27
6,676,618 B2 * 1/2004 Andersen ................. 602/7

* cited by examiner

*Primary Examiner*—Khanh Nguyen
*Assistant Examiner*—Saeed M Huda
(74) *Attorney, Agent, or Firm*—Arthur. W. Fisher, III

(57) ABSTRACT

A method of producing an orthotic brace or prosthetic device comprising the steps of creating an anatomical mold or cast of that portion of the patient's anatomy upon which the orthotic brace or prosthetic device is to be applied, applying at least one layer of epoxy resin over at least a portion of the anatomical mold, applying at least one layer of carbon graphite fabric on at least a portion of the layer of epoxy resin, placing the anatomical mold with the epoxy resin and carbon graphite fabric in an enclosure having an interior, heating the interior of the enclosure to melt the epoxy resin and reducing the pressure in the interior of the enclosure causing the melted epoxy resin to impregnate the carbon graphite fabric, and allowing the melted epoxy resin to harden in the carbon graphite fabric forming the orthotic brace or prosthetic device.

2 Claims, 8 Drawing Sheets

METHOD OF PRODUCING AN ORTHOTIC BRACE OR PROSTHETIC DEVICE

BACKGROUND OF THE INVENTION

1. Field of the Invention

A method of producing a prosthetic device or orthotic brace comprising impregnating a carbon graphite fabric with resin to form a rigid support 2. Description of the Prior Art Numerous efforts have been made to design and manufacture a light weight, durable orthotic brace. New materials now provide an opportunity to create new, more useful braces.

U.S. Pat. No. 5,817,041 shows a lower limb orthotic comprising a foot orthotic, a pair of lateral supporting members, a detached or removable anterior support member, a posterior support member, and strips of composite materials to resist plantar flexion, dorsiflexion and various of movements of the foot and ankle. The lateral supporting members further having strips of composite materials having fibers orientation substantially parallel to the length wise axis of the lateral supporting members. The foot orthotic and posterior supporting member further have composite strips extending across the bottom portion of the foot orthotic and rear side of the posterior supporting member respectively.

U.S. Pat. No. 5,693,007 teaches a method and apparatus for forming a custom fit knee orthotic including forming a flat preassembled knee orthotic of rigid carbon fiber and plastic resin composite material connected in a flat, rigid state by joint mechanisms.

U.S. Pat. No. 5,624,386 relates to an orthopedic brace using the shaped composite bars as integral components, and a method of thermoshaping the composite bars for use as filled components in the orthopedic brace are provided. The composite bars contain multiple fiber layers oriented in at least two directions with respect to the bar length to provide high flexural and torsional strength. The novel method of thermo-shaping yields improved results over prior thermo-shaping methods by providing an uncomplicated shaping capability while maintaining the structural and mechanical properties of the composite bar.

U.S. Pat. No. 5,573,501 shows a laminated, plastic orthotic device custom fitted to a wearer's extremity, typically a leg, wherein the orthotic includes a indicia bearing layer viewable on the outer surface of the orthotic. In one preferred embodiment, the device is fabricated from multiple layers of woven, reinforced and non-reinforced fabrics, adhesives, curable plastic resins and an image bearing layer. In other preferred embodiments, the device is fabricated of thermosetting plastic materials and an image bearing layer. The image layer may be comprised of woven fabric or non-woven materials which include drawings, insignias, photographs, textures or combinations thereof.

U.S. Pat. No. 5,154,690 discloses a supporter for mounting on a limb in position to cover an affected body portion to constrain and limit movement thereof comprising a tubular stretchable elastic material forming a main body and reinforcing member comprising an interlining laminated to a surface member which acts to restrict the elongation of said interlining.

U.S. Pat. No. 4,813,090 shows a hybrid composite material constructed from woven reinforced fabrics of Kevlar 49 and biaxially reinforced fibers of graphite and E-Glass bonded together with a thermosetting adhesive, for the application of custom orthotics. The material interlocks different fibers at different locations of the orthotic in order to take advantage of the unique properties of each reinforcing fibers. The resulting material creates a hybrid composite that exhibits a balance of properties, in both the longitudinal and transverse directions, unavailable with any single reinforcing fibers. A method of orthotic manufacturing involves a hand lat-up and forming procedure. The constructed composite material is formed and pressed on a prescribed cast, then allowed to cure under pressure. The post-cured material is stripped from the cast, then cut and ground and finally finished to the required orthotic. The produced orthotic combines the desired feature of a thin section with excellent combination of properties relevant to custom orthotics. Such properties include light weight, high strength and modulus, excellent resistance to impact, fatigue, and creep, and outstanding ability to damp vibrations.

U.S. Pat. No. 4,672,955 teaches the thigh and calf bands of a knee orthotic formed of a layer or layers or curable composite material. The sidebars are integral with the thigh and calf bands in that they are simply extensions of the layers forming the thigh and calf bands. The sidebars are cured prior to fitting the thigh and calf bands about the leg, but the thigh and calf bands are left incurred so that they may be formable about the leg and cured in place thereon.

U.S. Pat. No. 5,158,530 discloses a method of applying an orthopedic cast to an injured body portion consisting of braiding a tubular cast, in situ, around the injured body portion. A braiding machine applies the tubular braid of fibrous casting yarns around the injured body portion to form a braided cast which conforms to the shape of the injured body portion. The braided cast is then coated with a matrix material, which provides the necessary rigidity to the cast, yet allows the cast to breathe.

U.S. Pat. No. 3,682,163 shows a light weight, semi-rigid snap on orthopedic splint having a flexible sheet plastic main body laminated to a thick spongy layer and equipped with long shallow channels for the insertion of flexible reinforcing splints. The edges of the main body are provided with a suitable adjustable fastener as one having a multiplicity of L-shaped ribs which interlock selectively in different over-lapped positions as necessary to form a snug fit with a limb or any part of the body and notched crosswise of the ribs to adapt the splint for assembly about a tapering portion of the body as a limb.

U.S. Pat. No. 3,040,740 discloses a prefabricated article for incorporation under surgical casts and molds comprising a plurality of superimposed concentrically disposed seamless tubular layers of loosely knit cotton cloth. Each layer of cloth is formed of intercoupled threads in co-acting relationship with each other with certain threads intersecting other threads at juncture points forming oblique angles and defining open interstices therebetween with the distance between adjacent juncture points along any thread being greater than the diameter of any of the threads so that when pulled the layers of cloth will deform without stretching the intercoupled threads by having the juncture points which are generally aligned to the direction of pull separating a substantial amount in relation to each other and the juncture points which are generally aligned transversely to the direction of pull covering a substantial amount in relation to each other.

U.S. Pat. No. 5,020,523 relates to a splint device for splinting and immobilizing the lower leg, ankle, and foot including L-shaped inner core member having a slightly cupped heel portion, a horizontal basal portion extending frontally from the heel portion and a slightly curved vertical portion extending upwardly from the heel portion. A flexible foam cover is disposed on the core member to form a body of the splint device which is positionable against the lower leg, heel, and plantar surface of the foot, the cover being sized and configured to fully conceal the core member therewithin.

U.S. Pat. No. 5,282,483 shows a immobilizing apparatus for an injured body part including a rigid plate conforming to the injured body part and having two opposite faces, upon one of which the injured body part is provided; a limiting unit to limit the lateral movement of the injured body part on the rigid plate; an adjustable member by which the overall length of the rigid plate can be adjusted; and a fastening member to fasten the injured body part, immobilizing the injured body part on the rigid plate.

U.S. Pat. No. 5,593,383 discloses a securing apparatus for an ankle and foot orthotic brace. The brace is used for supporting and selective immobilization of a patient's ankle and foot. The brace has a multiple part L-shaped construction with a contoured leg support portion and a foot portion having a resilient interconnecting heel portion connected therebetween. The securing apparatus includes a foot pad with aperture tabs extending therefrom and being part of the foot portion. A fabric foot engagement enclosure is provided which secures to the foot pad by a plurality of adjustable fastening straps engaged through said apertures to the aperture tabs.

U.S. Pat. No. 5,799,659 relates to a device for treatment of foot and ankle conditions comprising a rigid, molded shell having a generally U-shaped cross-sectional configuration and a flat foot bed covered by a soft fabric covering. Removable and interchangeable foot bed wedge insert permits the angle of dorsiflexion, plantarflexion, inversion and eversion to be varied.

U.S. Pat. No. 5,897,515 shows a ankle-foot orthotic of a carbon fiber reinforced material having low weight is carried on the front of the lower leg, extending over the lateral ankle and preventing plantar flexion. The ankle-foot orthotic comprises a frame of thin flexible material extending over the front of the lower leg, anterior of the lateral ankle and beneath the sole of the foot and a supporting portion of rigid material extending over a narrow part of the front of the lower leg, anterior of the lateral ankle and beneath the part of the sole of the foot. The orthotic includes a fastening means for fastening the orthotic to the leg. In a preferred embodiment the orthotic comprises a substantially inflexible reinforcement element and a tough flexible element, the reinforcement element extending over a narrow part of substantially the whole frame and the flexible part extending over a substantial part of the sole of the foot. The frame is preferably made of thin flexible fiber glass reinforced plastic resin material. The reinforcement element is made of rigid carbon fiber reinforced plastic resin material. With the tough flexible element is preferably made of aramid fiber reinforced plastic resin.

U.S. Pat. No. 6,146,349 describes a copolymer thermoplastic natural foot orthotic for supporting and controlling the movement of a lower extremity. The orthotic is fabricated by forming a positive mold of the lower extremity and modifying the positive mold in predetermined locations to accomplish the type of lower extremity control desired. A strip of heated thermoformable copolymer material is strategically positioned around predetermined locations on the positive mold for providing increased support for the natural foot orthotic at these predetermined locations. A sheet of heated thermoformable copolymer material is then drape mold around the positive mold and copolymer strip wherein the copolymer sheet is vacuum sealed to conform to the shape of the positive mold. The copolymer sheet and copolymer strip are integrally formed into a single supporting structure. After the thermoformed copolymer sheet and strip have cooled, trimlines are made in the thermoformed copolymer sheet depending upon the lower extremity control desired wherein all excess material outside of the trimlines is removed. Utilizing modifications to the positive mold and strategically positioned trimlines in conjunction with the reinforcing copolymer strip, a natural foot orthotic is achieved that is lighter, cosmetically superior, dynamic and durable.

U.S. Pat. No. 6,676,618 teaches a ankle-foot orthotic made integrally from a thin, shaped lightweight material. The orthotic comprises a flat foot-supporting member for extending beneath the sole of a foot of a user, a calf abutment member for abutting the calf of the user, a narrow connecting member extending from the foot-supporting member at a location on one side, preferably the outer side, of the ankle of the user to the calf abutment member so as to interconnect the foot-supporting member and the calf abutment member, and a releasable fastener for fastening the calf abutment member to a leg of the user. The orthotic may be made by a method, in which a thermoplastic material with reinforcing fibers is arranged between opposite plastic films or foils in a desired mutual arrangement. Thereafter, the space defined between the opposite films is sealed, and air or gas is then removed from the sealed space so as to compact the material arranged therein and so as to form a blank. The blank thus formed is thereafter heated to a plasticizing temperature and formed into the desired shape.

G.B. Pat. No. 2,188,550 shows a calf band which is to pass around the leg, has a central portion connected to the upper end portion of a posterior leaf spring and two lateral portions which are to overlap in front of the leg and which are connected together by suitable means. The central portion provides a cushion between the upper end portion and the calf.

SUMMARY OF THE INVENTION

The present invention relates to a method or process of producing an orthotic brace or a prosthetic device constructed of an impregnated shell as described more fully hereinafter.

Generally, the impregnated shell comprises at least one layer of fabric or material impregnated with a hardened structural resin to form a contoured inner contact surface conforming to a portion of the patient's anatomy.

The method of producing the orthotic brace or prosthetic device comprises the steps of:

creating an anatomical mold or cast of that portion of the patient's anatomy upon which the orthotic brace or prosthetic device is to be applied;

applying at least one inner layer of separation material to at least a portion of the surface of the anatomical mold or cast;

applying at least one layer of epoxy resin to at least a portion of the separation material;

applying at least one layer of substrate shell forming fabric or material to at least a portion of the surface of the epoxy resin;

applying at least one outer layer of separation material to at least a portion of the substrate shell forming fabric;

ventilating the outer layer of separation material;

placing the enclosed anatomical mold or cast in a treatment chamber;

creating a vacuum in the treatment chamber;

heating the interior of the treatment chamber to melt the epoxy resin and impregnate the substrate shell forming fabric with liquid epoxy resin;

curing the epoxy resin thereby forming a hardened prosthetic device or orthotic brace.

removing the anatomical mold or cast from the treatment chamber;

removing the epoxy resin impregnated shell from the anatomical mold or cast; and The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which.

Similar reference characters refer to similar parts throughout the several views of the drawings.

DETAILED DESCRIPTION OF THE INVENTION

Figure 1:
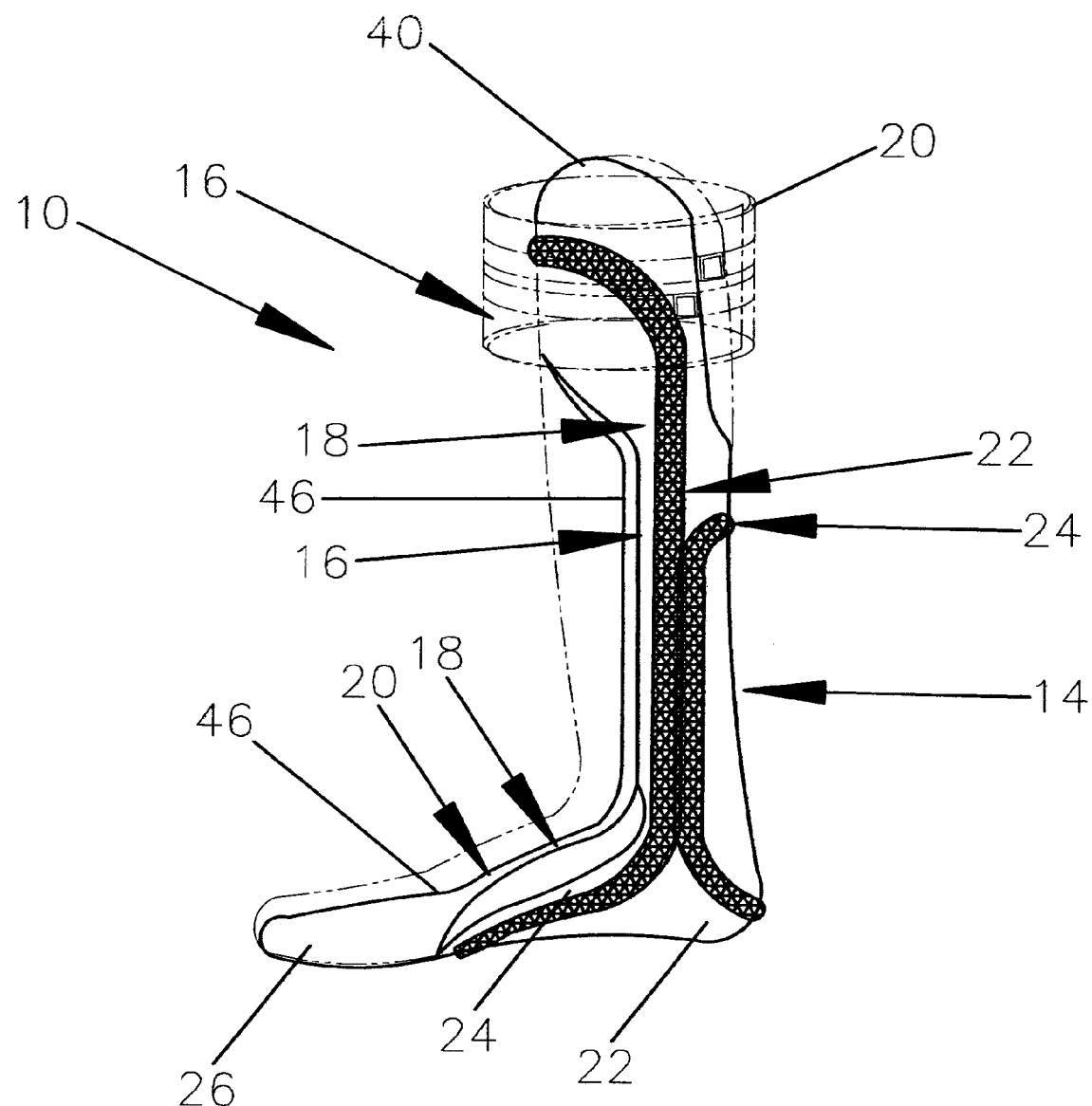
FIG. 1 is a side view of an orthotic brace comprising a lower limb or leg orthotic brace produced using the method or process of the present invention.
Figure 2:
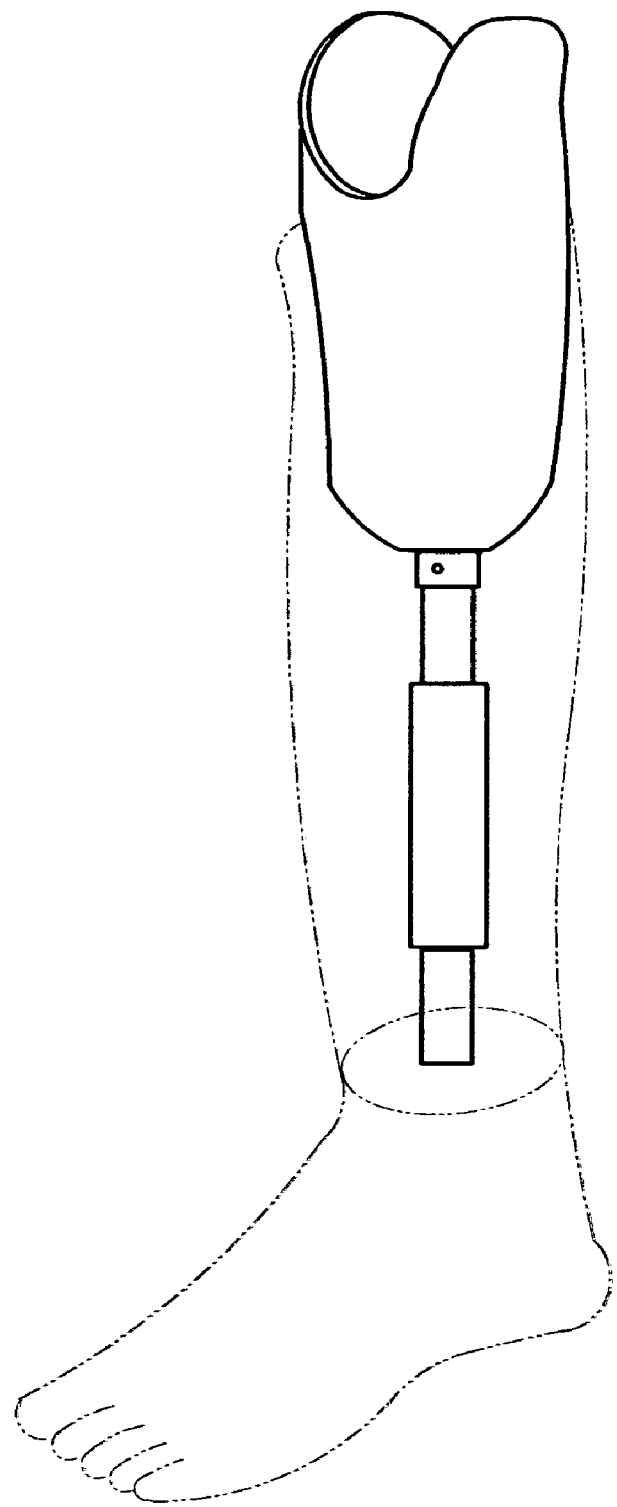
FIG. 2 is a perspective view of a prosthetic device comprising a knee cup produced by using the method or process of the present invention.

The present invention relates to a method or process of producing an orthotic brace generally indicated as 10 in FIG. 1 or a prosthetic device generally indicated as 12 in FIG. 2. Both the orthotic brace 10 and the prosthetic device 12 are constructed of an impregnated fabric or shell as described more fully hereinafter.

Figure 3:
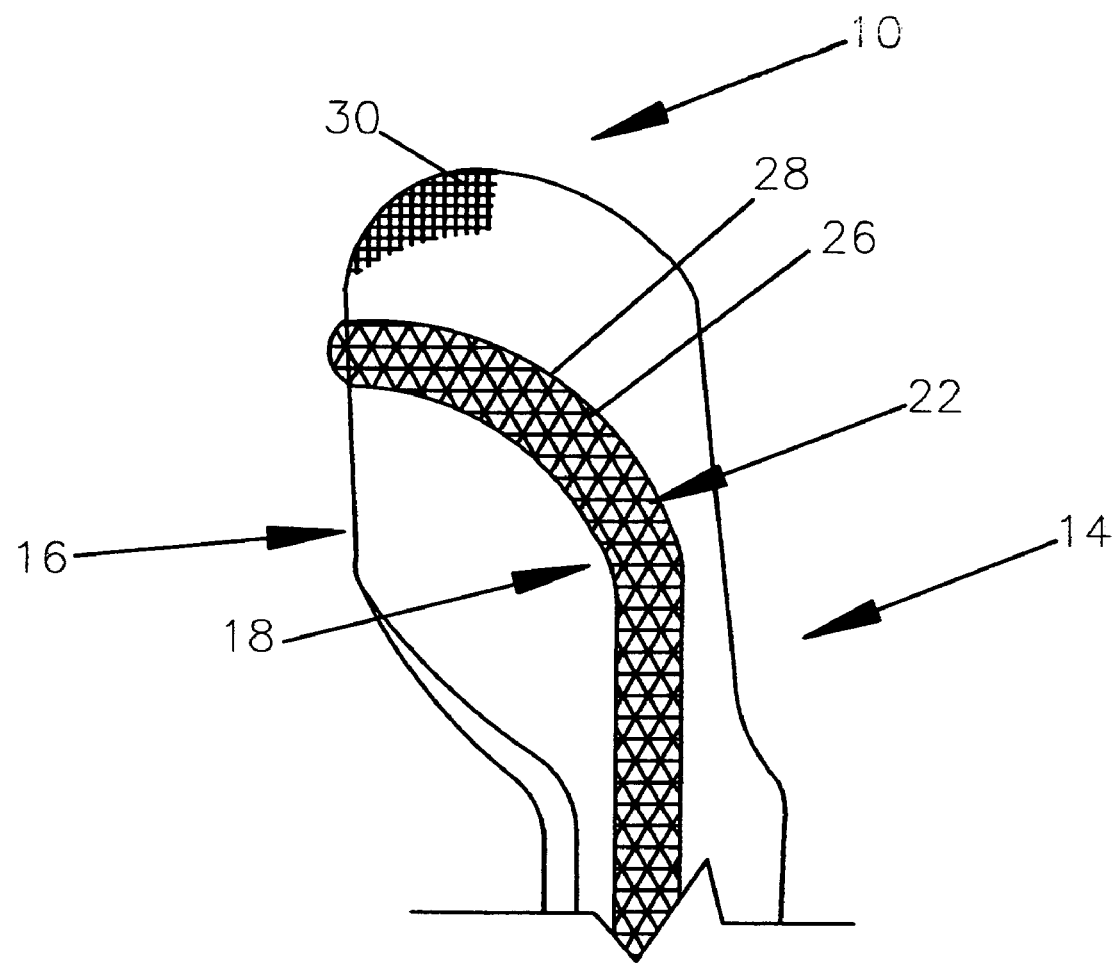
FIG. 3 is a partial detailed side view of an orthotic brace comprising a lower limb or leg orthotic brace produced using the method or process of the present invention.

As shown in FIGS. 1 and 3, the orthotic brace 10 may comprise a lower limb orthotic brace generally indicated as 14 for controlling the movement of the knee, ankle and foot of a patient. The lower limb orthotic brace 14 comprises a shaped substrate or contoured orthotic shell generally indicated as 16 having a load-bearing frame generally indicated as 18 integrally formed therewith. The lower limb of the patient (not shown) is retained therein by a flexible strap 20.

The load-bearing frame 18 includes a support member generally indicated as 22 comprising a fabric impregnated with an epoxy resin to produce a hardened structure. Additional support members 24 may be positioned high-stress areas of the contoured orthotic contact shell 16 to reduce the amount of flexure therein.

Specifically, as best shown in FIG. 3, the fabric of the support members 22 and 24 may comprise a plurality of fibers 26 may be woven together in a tubular multidirectional braid 28 to be impregnated with the epoxy resin. The fabric may also be a sheet or panel of fibers as described hereinafter. The fabric 22 and 24, and the fibers 26 may comprise graphite, carbon, Kevlar, fiberglass or other commercially available materials. The epoxy resin comprises an oven curable expoxy resin.

Generally, the contoured orthotic contact shell 16 comprises at least one layer of fabric 30 impregnated with a hardened structural resin to form a contoured inner contact surface conforming to the outer surface of the patient's lower limb. The contoured orthotic contact shell 16 is constructed by applying fabric 30 to a positive cast of the patient's lower limb. The tubular multidirectional braid 28 is then compressed into a substantially flat strip against the outer surface of the contoured orthotic contact shell 16 and placed within an enclosure. A vacuum and heat are then applied to the interior of the enclosure melting the epoxy resin into the tubular multidirectional braid 28. As the epoxy resin impregnates the fabric 30 and the tubular multidirectional braid 28, the inner side of the tubular multidirectional braid 28 is maintained in continuous contact with the outer surface of the contoured orthotic contact shell 16 along the entire length of the tubular multidirectional braid 28. The epoxy resins impregnating the tubular multidirectional braid 28 combine with the epoxy resin impregnating the fabric 40 forming a continuous bond between the flattened tubular multidirectional braid 28 and the fabric 40 throughout the length of the support member 22.

An additional layer of fabric 40 may be applied over the contoured orthotic contact shell 16 and the integral load-bearing frame 18 to increase the bond between the integral load-bearing frame 18 and the contoured orthotic contact shell 16 or the support member 22. Pigments may also be added to the structural resins prior to introduction to the process in order to mimic skin tone or to create other decorative effects. After the resins impregnating the fabric 40 and braided tube 28 have hardened, the positive cast is removed by cutting away portions of the fabric 40 without invading the braid 28 or severing any of the bundled continuous composite fibers 26 therein.

The prosthetic device 12 may comprise a knee cup contoured to cover the lower portion of the upper leg as shown in FIG. 2. The contoured knee cup is similarly constructed with similar components or elements bearing similar numerical designations.

The method of producing the orthotic brace 10 or the prosthetic device 12 comprises the steps of:

creating an anatomical mold or cast of that portion of the patient's anatomy upon which the orthotic brace 10 or prosthetic device 12 is to be applied;

cleaning or smoothing the outer surface of the anatomical mold or cast shaving or flattening a portion of the posterior of the anatomical mold or cast;

applying at least one inner layer of nonstick separation material to at least a portion of the surface of the anatomical mold or cast;

applying at least one layer of epoxy resin to at least a portion of the nonstick separation material;

a applying at least one layer of substrate shell forming fabric to at least a portion of the surface of the epoxy resin;

applying at least one outer layer of nonstick separation material to at least a portion of the substrate shell forming fabric;

ventilating the outer layer of nonstick separation material;

applying at least one layer of a first porous material to the ventilated outer layer of nonstick separation material;

applying at least one layer of a second porous material to the layer of first porous material;

placing the anatomical mold or cast into a heat resistance enclosure;

placing the enclosed anatomical mold or cast in a treatment chamber;

creating a vacuum in the treatment chamber;

heating the interior of the treatment chamber to melt the epoxy resin and impregnate the substrate shell forming fabric with liquid epoxy resin;

allowing the resin impregnated shell to harden;

removing the anatomical mold or cast from the treatment chamber;

removing the layers of the first and second porous material and the outer layer of nonstick separation material from the resin impregnated shell;

removing the resin impregnated shell from the anatomical mold or cast;

shaping the resin impregnated shell to form the orthotic brace 10 or the prosthetic device 12.

Figure 4:
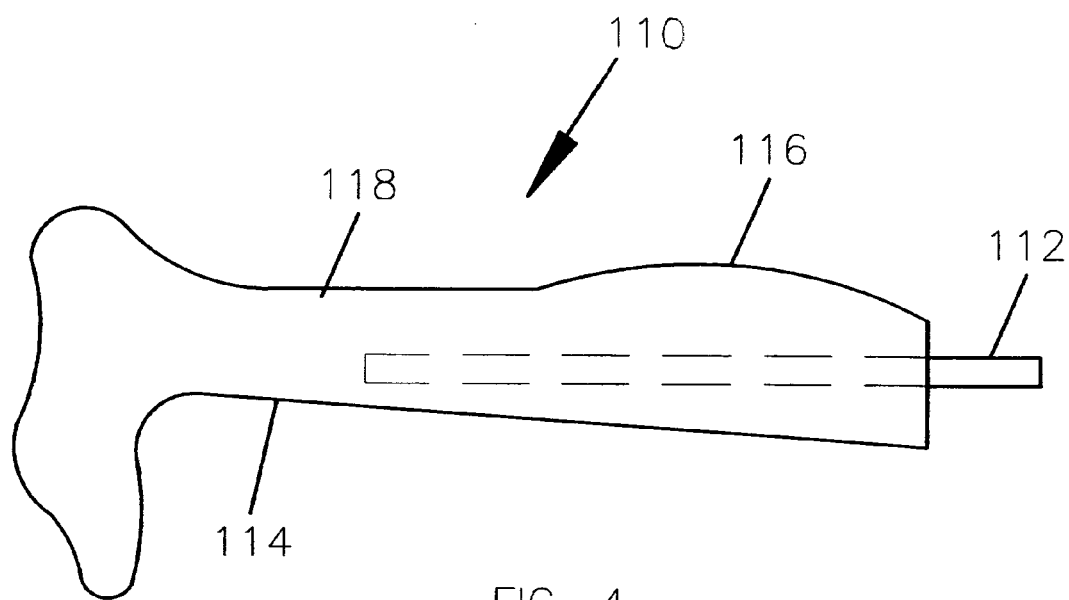
FIGS. 4 through 11 show the sequence of steps of the method or process of the present invention.
Figure 5:
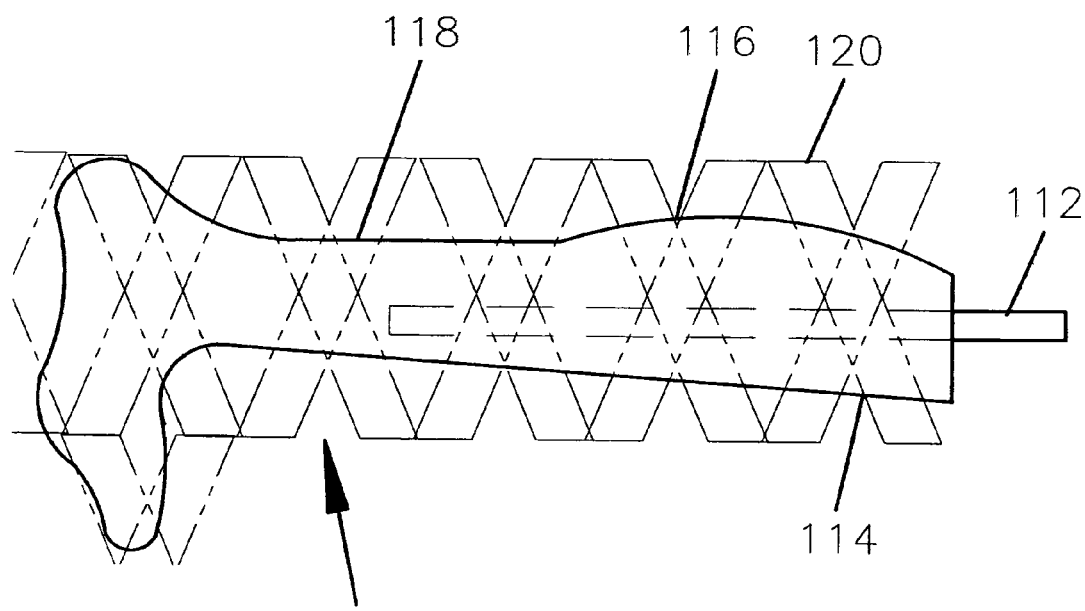
Figure 6:
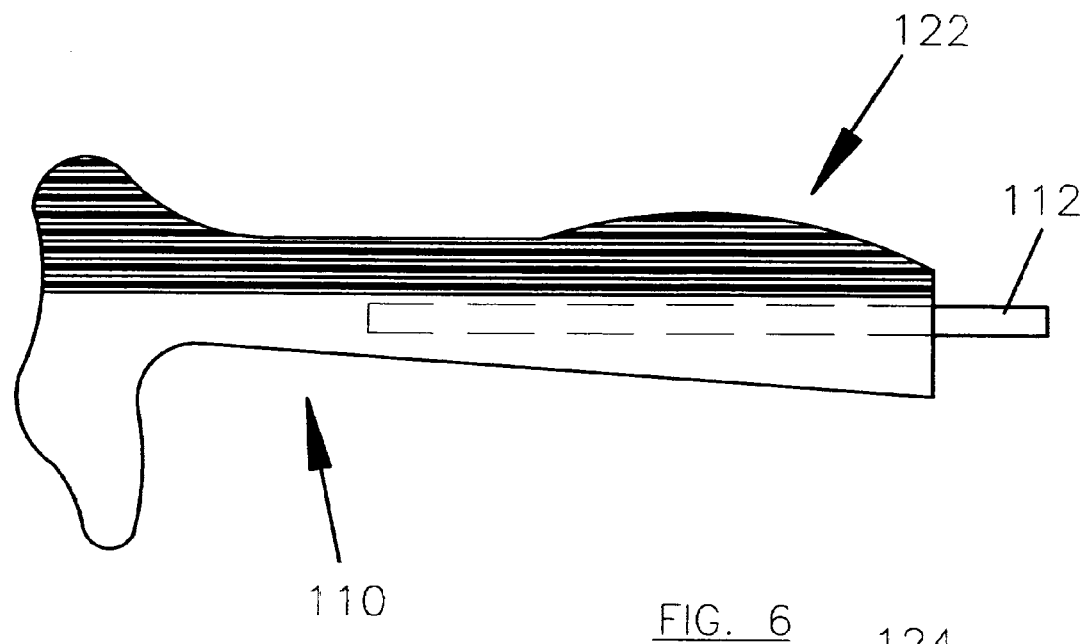
Figure 7:
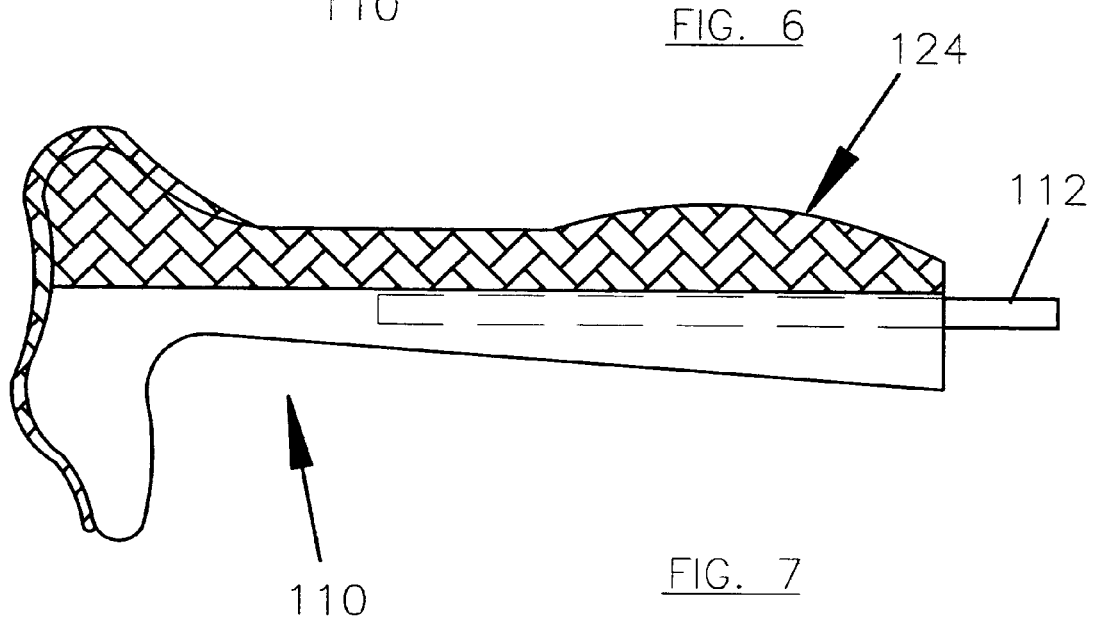
Figure 8:
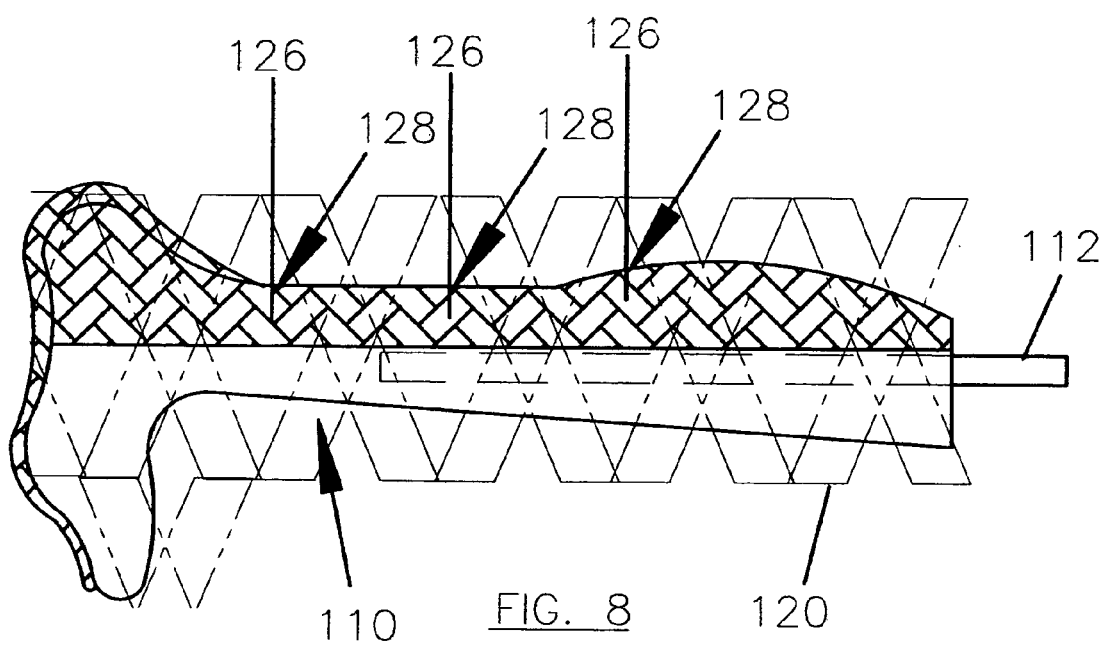

The method of producing the orthotic brace 10 or the prosthetic device 12 of the present invention is best understood with reference to FIGS. 4 through 11. For example, as shown in FIG. 4, an anatomically shaped plaster mold or cast such as a lower leg or limb generally indicated as 110 including a handle 112 is created or formed. The outer surface 114 is sanded and cleaned. A portion of the posterior 116 of the anatomically shaped plaster mold or cast 110 may be shaved or cut to form a substantially flat area 118. As shown in FIG. 5, at least one inner layer of nonstick separator or cast covering material such as polyethylene film or tape 120 is applied to at least a portion of the outer surface 114 of the anatomically shaped plastic mold or cast 110. The preferred method comprises applying five layers of nonstick separator or cast covering material 120. As shown in FIG. 6, at least one layer of epoxy resin 122 is applied to at least a portion of the outer surface of the nonstick separator or cast covering material 120. Multiple layers of epoxy resin may be applied depending on the desired strength or thickness of the shell. Next, at least one layer of substrate shell forming fabric 124 is applied to at least a portion of the outer surface of the epoxy resin 122 as shown in FIG. 7. The preferred method comprises applying two layers of substrate shell forming fabric 124. As shown in FIG. 8, at least a portion of the outer surface of the substrate shell forming fabric 124 is covered by at least outer one layer of nonstick separation material such as polyethylene film or tape 120. The preferred method comprises applying five layers of nonstick separation material 120. The outer layer(s) of nonstick separation material 120 are ventilated by piercing or penetrating with a pin, knife or similar instrument 126 to form a plurality of aperture each indicated as 128 therethrough.

Figure 9:
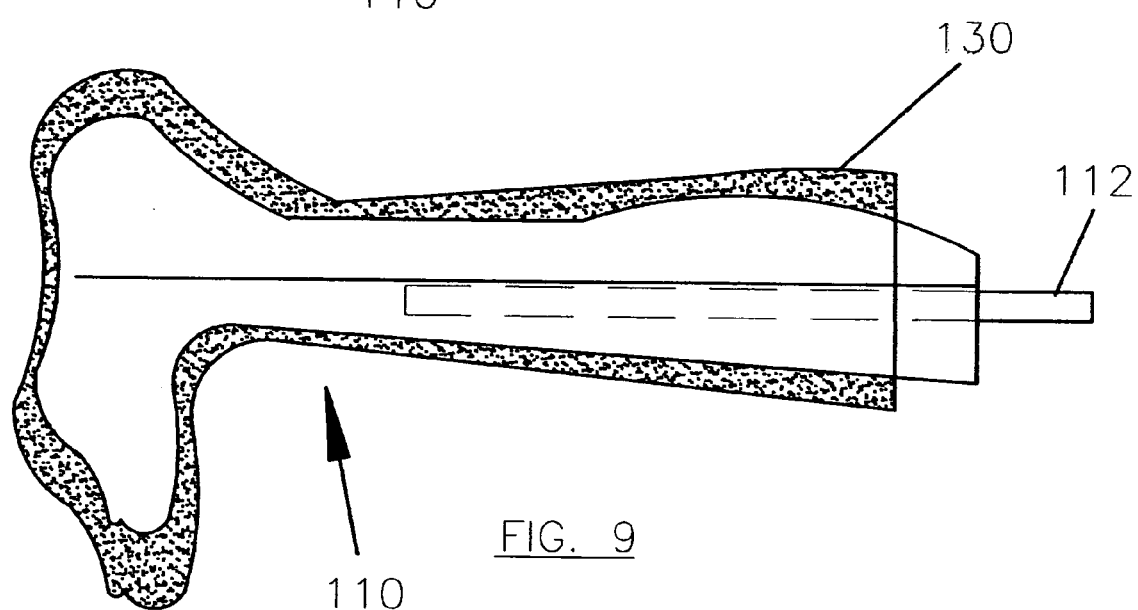
Figure 10:
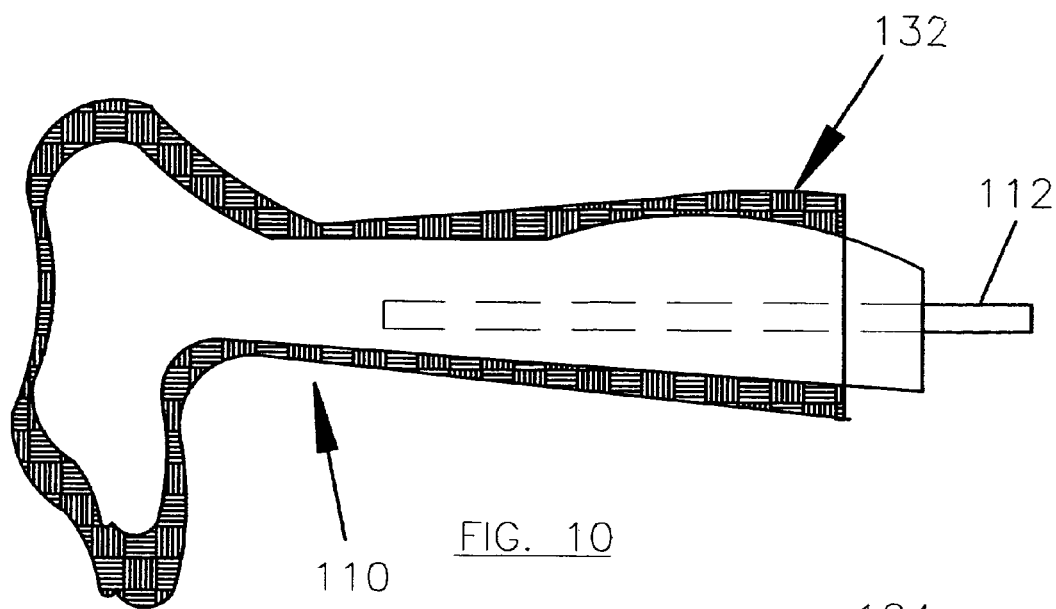
Figure 12:
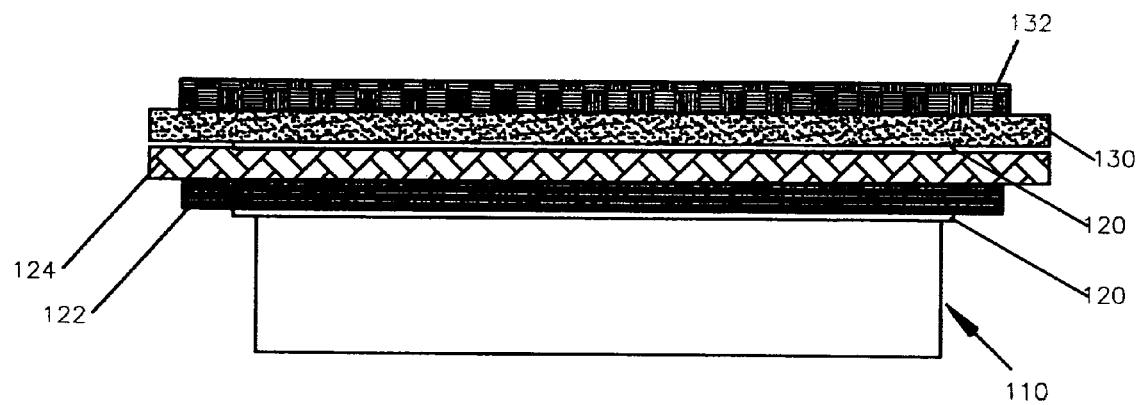
FIG. 12 shows a cross-sectional view of the various layers of material included in the method or process of the present invention.

As shown in FIGS. 9 and 10, a first layer of porous material 130 and then a second layer of porous material 132 are applied to the anatomically shaped plaster mold or cast 110. FIG. 12 is a cross-sectional view of layers of material applied in sequence to the anatomically shaped plaster mold or cast 110.

Figure 11:
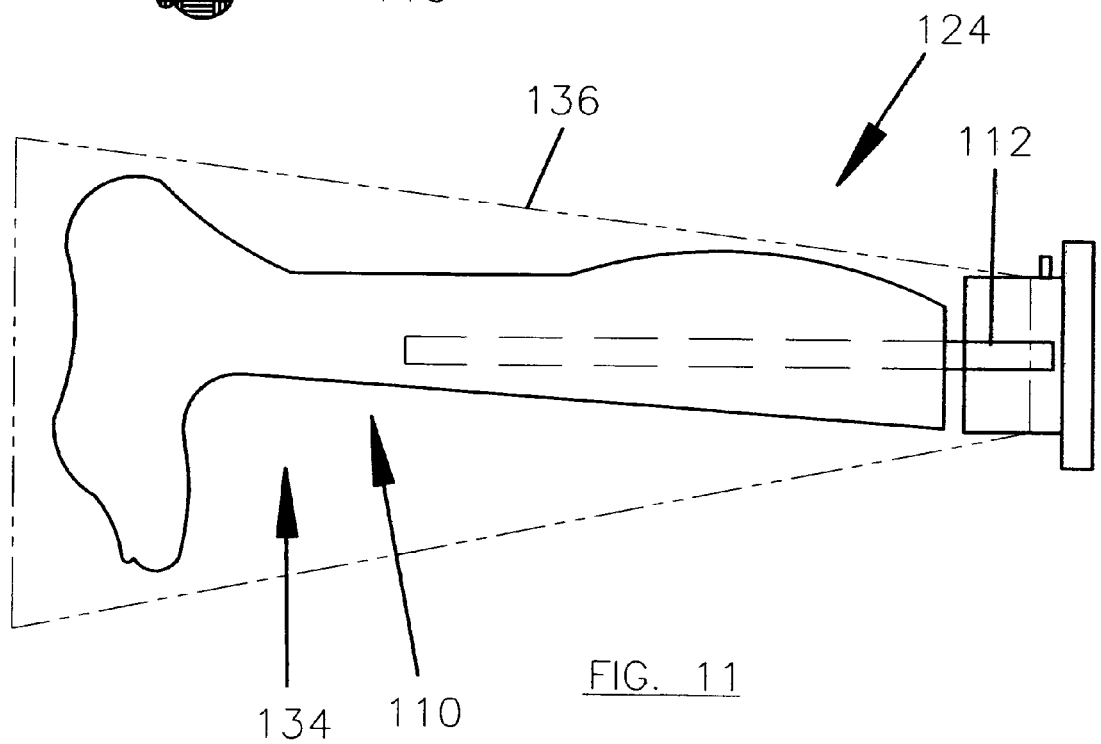

Once so prepared, the anatomically shaped plaster mold or cast 110 is placed in a heat resistance enclosure or bag and placed in a treatment chamber 134 within an oven or enclosure 136 as shown in FIG. 11. The treatment chamber 134 is held at a vacuum and heated to at least about 220 degrees Fahrenheit for at least about 100 minutes to melt the epoxy resin 122 to impregnate the substrate shell forming fabric 124. The anatomical mold or cast is removed from the treatment chamber and the layers of the first and second porous material and the outer layer of nonstick separation material are removed from the resin impregnated shell. The resin impregnated shell is then removed from the anatomical mold or cast.

Figure 13:
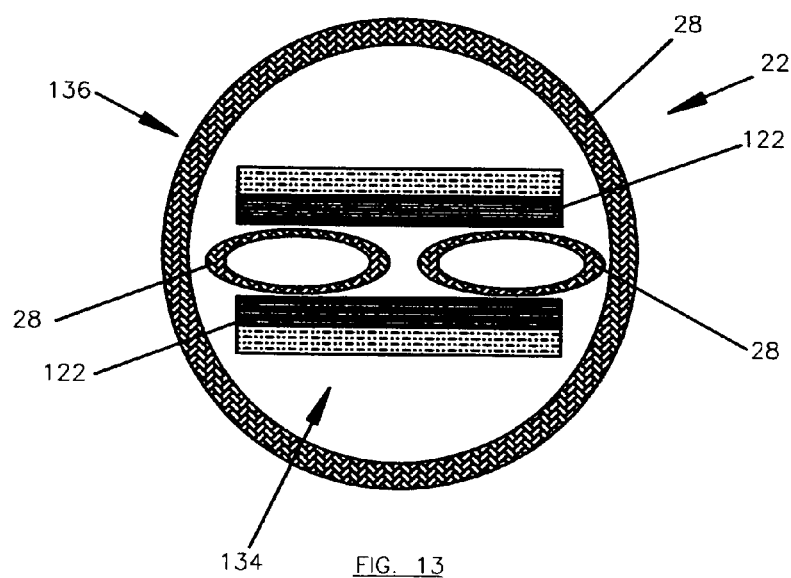
FIG. 13 shows a cross-sectional view of an alternative embodiment of the substitute shell forming fabric used in the method or process of the present invention.

FIG. 13 shows an alternate embodiment of a support member 22. The inner core 134 comprises a pair of inner tubular multidirectional braids 28 disposed between layers of epoxy resin 122 disposed between layers of porous material; while, the outer casing comprises an outer tubular multidirectional braid 28 comprising an inner core generally indicated as 134 disposed within an outer casing generally indicated as 136.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. The method of producing the orthotic brace comprising an orthotic shell having a load bearing frame integrally formed therewith, said method comprising the steps of:

creating an anatomical mold or cast of that portion of the patient's anatomy upon which the orthotic brace or prosthetic device is to be applied;

applying at least one inner layer of nonstick separation material to at least a portion of the surface of the anatomical mold or cast;

applying at least one layer of epoxy resin to at least a portion of the nonstick separation material;

applying at least one layer of substrate shell forming fabric to at least a portion of the surface of the epoxy resin;

compressing an elongated load bearing frame forming multidirectional braid member longitudinally against a portion of the outer surface of said layer of substrate shell forming fabric;

applying at least one outer layer of nonstick separation material to at least a portion of the substrate shell forming fabric;

ventilating the outer layer of nonstick separation material;

applying at least one layer of a first porous material to the ventilated outer layer of nonstick separation material;

placing the anatomical mold or cast into a heat resistance enclosure;

placing the enclosed anatomical mold or cast in a treatment chamber;

creating a vacuum in the treatment chamber;

heating the interior of the treatment chamber to melt the epoxy resin and impregnate the substrate shell forming fabric with liquid epoxy resin;

allowing the resin impregnated shell to harden;

removing the anatomical mold or cast from the treatment chamber;

removing the layer of the first porous material and the outer layer of nonstick separation material from the resin impregnated shell and elongated multidirectional braid member;

removing the resin impregnated shell and elongated multidirectional braid member from the anatomical mold or cast;

shaping the resin impregnated shell and elongated multidirectional braid to form the orthotic brace or the prosthetic device.

2. The method of producing the orthotic brace comprising an orthotic shell having a load bearing frame integrally formed therewith, said method comprising the steps of:

creating an anatomical mold or cast of that portion of the patient's anatomy upon which the orthotic brace or prosthetic device is to be applied;

applying at least one inner layer of nonstick separation material to at least a portion of the surface of the anatomical mold or cast;

applying at least one layer of epoxy resin to at least a portion of the nonstick separation material;

applying at least one layer of substrate shell forming fabric to at least a portion of the surface of the epoxy resin;

compressing an elongated load bearing frame forming multidirectional braid member comprising an inner core including a pair of inner tubular multidirectional braids disposed between layers of epoxy resin disposed between layers of porous material disposed within an outer casing including an outer tubular multidirectional braid longitudinally against a portion of the outer surface of said layer of substrate shell forming fabric;

applying an additional layer of fabric over said layer of substrate contoured orthotic shell forming fabric and said elongated load-bearing frame forming multidirectional braid member to increase the bond therebetween;

applying at least one outer layer of nonstick separation material to at least a portion of the substrate shell forming fabric;

ventilating the outer layer of nonstick separation material;

applying at least one layer of a first porous material to the ventilated outer layer of nonstick separation material;

placing the anatomical mold or cast into a heat resistance enclosure;

placing the enclosed anatomical mold or cast in a treatment chamber;

creating a vacuum in the treatment chamber;

heating the interior of the treatment chamber to melt the epoxy resin and impregnate the substrate shell forming fabric with liquid epoxy resin;

allowing the resin impregnated shell to harden;

removing the anatomical mold or cast from the treatment chamber;

removing the layer of the first porous material and the outer layer of nonstick separation material from the resin impregnated shell and elongated multidirectional braid member;

removing the resin impregnated shell and elongated multidirectional braid member from the anatomical mold or cast;

shaping the resin impregnated shell and elongated multidirectional braid to form the orthotic brace or the prosthetic device.

* * * * *